US00PP28449P2

(12) United States Plant Patent
Freyre

(10) Patent No.: US PP28,449 P2
(45) Date of Patent: Sep. 26, 2017

(54) ***RUELLIA* PLANT NAMED 'R12-2-1'**

(50) Latin Name: *Ruellia simplex*
Varietal Denomination: R12-2-1

(71) Applicant: Florida Foundation Seed Producers, Inc., Marianna, FL (US)

(72) Inventor: Rosanna Freyre, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 14/999,630

(22) Filed: Jun. 7, 2016

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

(56) References Cited

U.S. PATENT DOCUMENTS

PP24,422 P3 5/2014 Freyre

*Primary Examiner* — Annette Para
(74) *Attorney, Agent, or Firm* — Christopher & Weisberg, P.A.

(57) ABSTRACT

'R12-2-1' is a new *Ruellia* cultivar distinguished by having excellent landscape performance, violet flowers, medium plant height, profuse branching, and no fruiting, as disclosed.

2 Drawing Sheets

ACKNOWLEDGMENT OF FEDERAL RESEARCH SUPPORT

The U.S. government has certain rights in this invention, pursuant to TSTAR Grant No. 00093296 awarded by the U.S. Department of Agriculture.

Genus and species: *Ruellia simplex*.

Cultivar denomination: 'R12-2-1'.

CROSS-REFERENCE TO RELATED APPLICATION n/a

BACKGROUND OF THE NEW CULTIVAR

The present invention relates to a new and distinct cultivar of *Ruellia* plant, botanically known as *Ruellia simplex*, hereinafter referred to by the name 'R12-2-1'.

*Ruellias* (also referred to as *Ruellia* plants) are flowering plants in the acanthus family (Acanthaceae). Flowers are typically trumpet shaped and blue, purple, pink, or white in color. *Ruellia* plants are evergreen perennials growing to about three feet tall with groups of stalks and lance-shaped leaves of about six to 12 inches long.

The new *Ruellia* cultivar 'R12-2-1' is a tetraploid individual that originated from a manual hybridization conducted on Feb. 16, 2012 in Gainesville, Fla., between breeding lines 'RU64'×'37-3-1-6'. 'RU64' is a white-flowered, tetraploid plant. '37-3-6-1' is a tetraploid plant with white flowers and purple corolla tube obtained from selfing clone '37-3-6'. '37-3-6' clone is a seedling of 'RU15', which is a diploid plant with white flowers and purple corolla tube. The apical meristem of '37-3-6' was treated with three applications of a 50 μM oryzalin solution every 12 hours.

'R12-2-1' has been reproduced asexually for over three years through vegetative cuttings at the Environmental Horticulture Research Greenhouses, located at the University of Florida, Gainesville, Fla. 32611 and has been shown to retain its distinctive characteristics through successive asexual propagations.

Plant Breeder's Rights for this cultivar have not been applied for. 'R12-2-1' has not been made publicly available more than one year prior to the filing date of this application.

SUMMARY OF THE INVENTION

The new *Ruellia* cultivar has not been observed under all possible environmental conditions. The phenotype may vary somewhat with variations in environment such as temperature, light intensity, water status, fertilizer rate and type, without, however, any variance in genotype.

The following are the most outstanding and distinguishing characteristics of 'R12-2-1' when grown under normal horticultural practices in Northwestern, North Central and Southwestern Florida, USA.

1. Excellent performance under a full sun environment;
2. Large violet flowers;
3 Mature plant height averaging 81 cm;
4. Profuse branching; and
5. No fruit production.

DESCRIPTION OF THE FIGURES

This new *Ruellia* cultivar is illustrated by the accompanying photographs which show the plant's form and foliage. The colors shown are as true as can be reasonably obtained by conventional photographic procedures.

DETAILED BOTANICAL DESCRIPTION OF THE CULTIVAR

Figure 1:
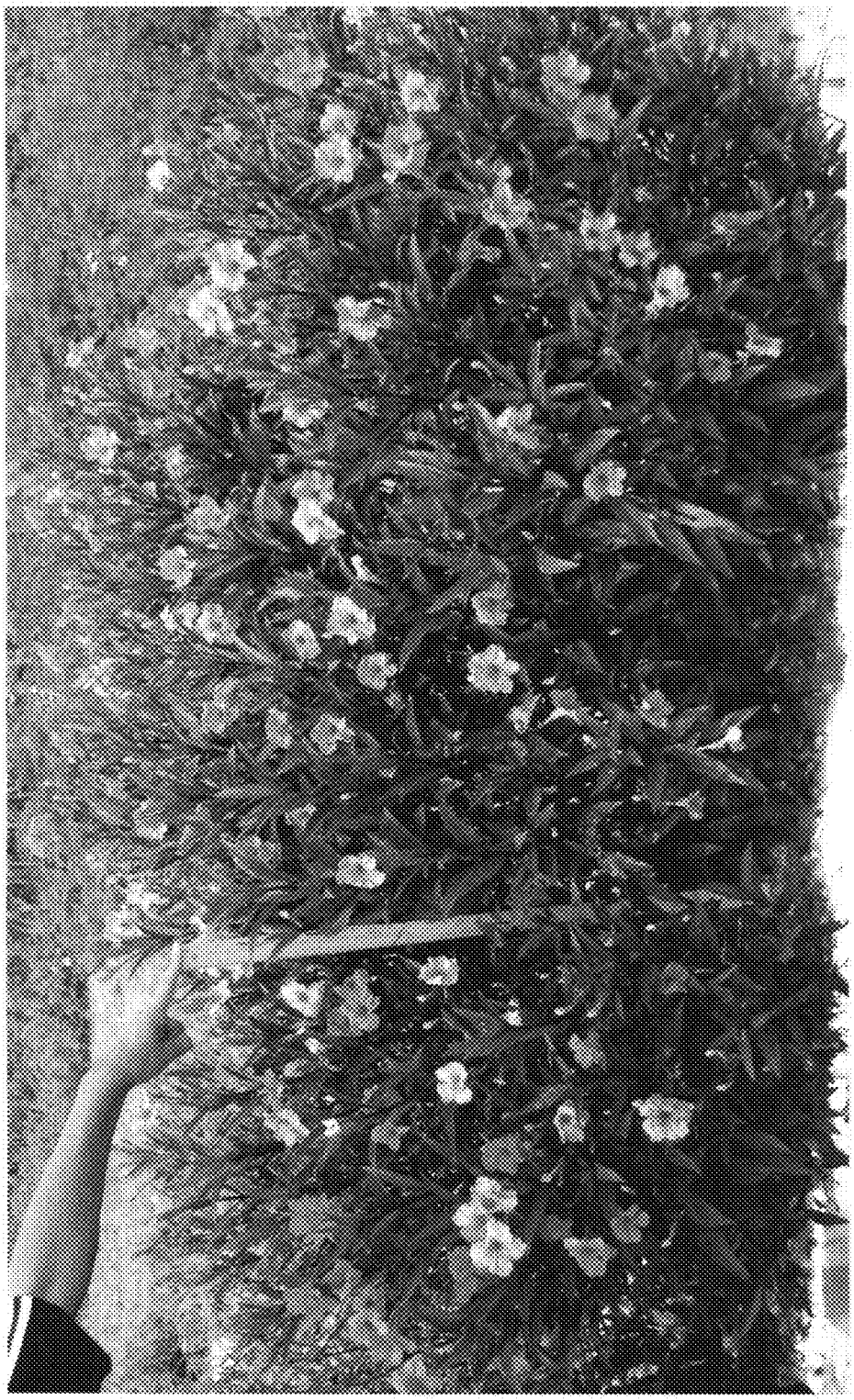
FIG. 1 shows a plot of three plants of *Ruellia simplex* 'R12-2-1' on Sep. 9, 2015, at the Plant Science Research and Education Unit (PSREU) in Citra, Fla.
Figure 2:
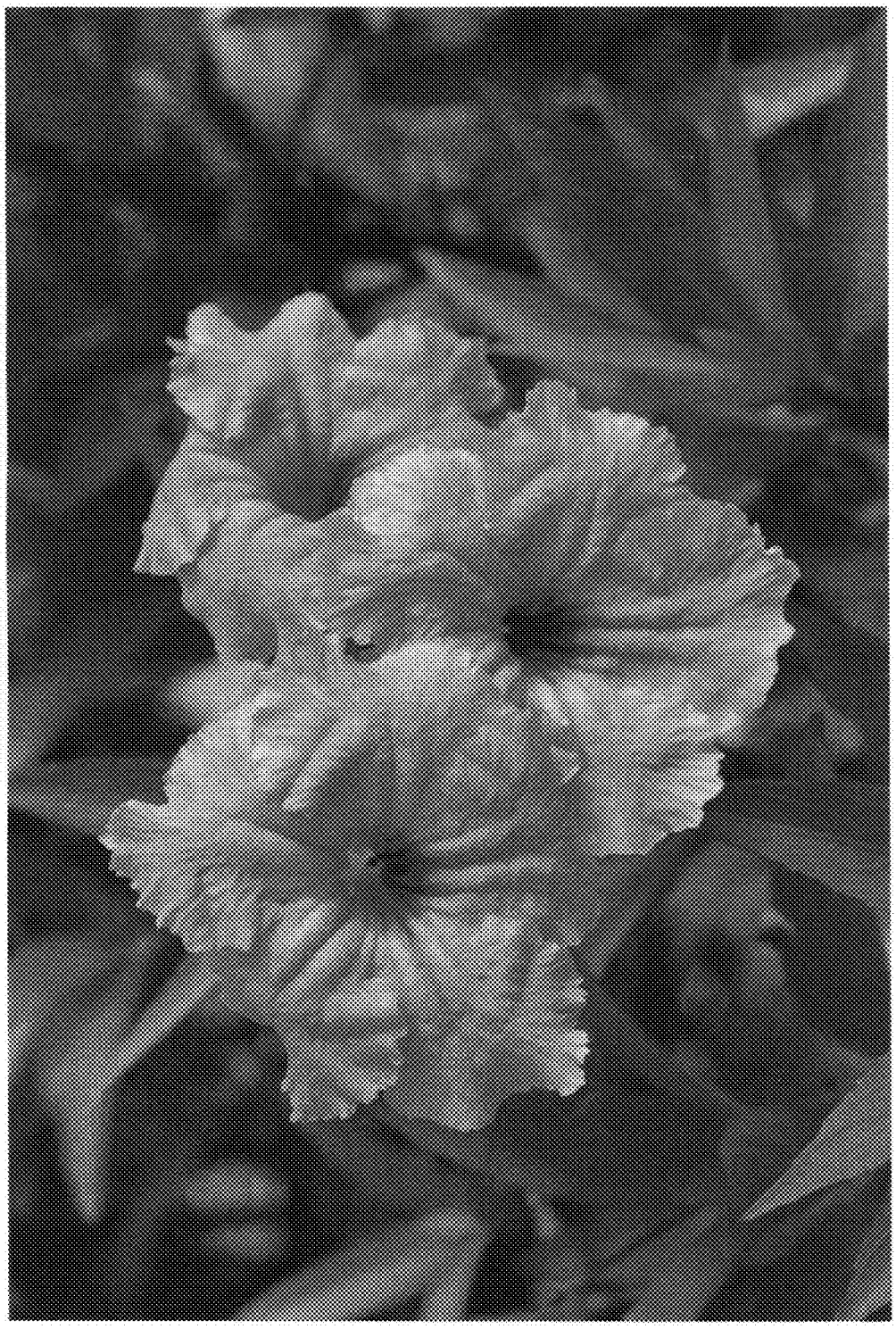
FIG. 2 shows flowers on *Ruellia simplex* 'R12-2-1' on May 2, 2016 at the Environmental Horticulture Research Greenhouses, University of Florida, Gainesville, Fla.

The following detailed description sets forth the distinctive characteristics of 'R12-2-1', also shown in FIGS. 1 and 2.

FIG. 1 shows a whole-plant photograph that was taken from 21-week-old plants grown in ground beds with drip irrigation at the Plant Science Research and Education Unit in Citra, Fla.

The flower photograph shown in FIG. 2 was taken from a 17-week-old plant grown at the Environmental Horticulture Research Greenhouses, University of Florida, Gainesville, Fla.

DESCRIPTION OF GROWING CONDITIONS

To botanically characterize 'R12-2-1', plants were propagated by cuttings and grown in a research greenhouse in Gainesville, Fla. Plants were approximately 17 weeks of age when flower and reproductive organ descriptions were measured. All colors were determined based on comparison with The Royal Horticultural Society Colour Chart (Royal Horticultural Society, 1995). All other measurements were obtained in simultaneous field trials conducted at Quincy (northwest Fla., 30.5° N, 84.6° W, AHS heat zone 9, USDA hardiness zone 8b), at Citra (north central Fla., 29.4° N, 82.2° W, AHS heat zone 10, USDA hardiness zone 9a) and at Wimauma (southwest Fla., 27.45° N, 82.1° W, AHS heat zone 10, USDA hardiness zone 9b). Measurements were done on field plants that were 21 weeks in age, on a total of 27 plants (9 plants per location, grown between May 11 to Aug. 30, 2015), and then averaged.

BOTANICAL DESCRIPTION

Botanical classification:
- *Family*.—Acanthaceae.
- *Botanical name*.—*Ruellia simplex*.
- *Common name*.—*Ruellia*, Mexican Petunia.
- *Cultivar*.—'R12-2-1'.

Plant description:
- *Form*.—Erect.
- *Habit*.—Clumping.
- *Height* (*from top of soil*).—81 cm.
- *Width* (*horizontal plant diameter*).—73 cm.

Parentage:
- *Female or seed parent*.—'RU64' (not patented).
- *Male or pollen parent*.—'37-3-6-1' (not patented).

Propagation:
- *Type cuttings*.—Vegetative meristems having at least two nodes.
- *Time to initiate roots*.—4 to 6 days.
- *Time to produce a rooted cutting*.—7 to 10 days.
- *Root habit*.—Adventitious (fibrous).
- *Root description*.—Callus forms in 3 to 4 days. Roots initiate in 5 to 8 days and become a highly branched cutting in 14 to 21 days.

Branches:
- *Quantity per plant*.—Average 62 per plant (with no pinching).
- *Branch color*.—Brown (RHS 200A) with a purple tint (RHS 187B) when mature. New growth is lighter in color (RHS 138B) and progressively gets darker with age.
- *Texture*.—Smooth.
- *Pubescence*.—Slightly tomentose, especially at nodes. RHS 155D (white).
- *Stem description*.—Round to square-shaped stem.
- *Branch diameter*.—1 cm at the base of a 40 cm long branch.
- *Branch length*.—88 cm maximum.
- *Internode length*.—5 cm on average.
- *Anthocyanin*.—RHS 183B (grey/purple).

Leaves:
- *Quantity of leaves per branch*.—15 to 25.
- *Arrangement*.—Decussate (opposite pairs).
- *Fragrance*.—None.
- *Shape*.—Lanceolate to elliptic.
- *Length*.—8.5 cm.
- *Width*.—1.7 cm.
- *Apex*.—Narrowly acute.
- *Base*.—Attenuate.
- *Margin*.—Entire.
- *Leaf texture* (*both surfaces*).—Slightly coriaceous.
- *Pubescence color* (*both surfaces*).—Not present.
- *Venation color*.—Upper surface: RHS 139A (green). Lower surface: RHS 137C (green).
- *Venation pattern*.—Pinnate.
- *Color, mature and immature leaf*.—Upper surface: RHS 147A (green). Lower surface: RHS 137C (green).
- *Petiole length*.—1.5 cm to 1.7 cm.
- *Petiole diameter*.—0.2 cm.
- *Petiole color*.—RHS 187A (grey).

Flowers and seeds:
- *Flower*.—Arrangement: Axillary in solitary or several-flowered cyme. Aspect: Actinomorphic corolla with 5 rounded petals; funnel form. Flowering habit (length of flowering season): April to October (North Florida). Number of inflorescences per plant: 1-10 cymes with 1 to 20 open flowers. Fragrance: Very mild and slightly sweet. Lastingness of individual bloom: 1 day. Rate of opening: Daily.
- *Flower bud*.—Shape: Elliptic. Length: 4.5 cm. Diameter: 1.0 cm. Color: RHS 77C (purple). Texture: Glandular with trichomes.
- *Corolla*.—Arrangement: Actinomorphic salverform (funnel form). Length: 4-6 cm. Diameter: 5-6.5 cm. Color: Upper surface: RHS 87B (violet). Lower surface: RHS 87B (violet). Corolla tube: RHS 86A (darker violet).
- *Banner*.—Length: Banner not present. Width: Banner not present. Apex: Banner not present. Base: Banner not present.
- *Margin*.—Texture (both surfaces): Smooth. Color: Upper surface: RHS 87A (violet). Lower surface: RHS 87C (violet).
- *Keel*.—Length: Keel not present. Width: Keel not present. Apex: Keel not present. Base: Keel not present. Margin: Keel not present Color: Keel not present.
- *Calyx*.—Number of sepals per flower: 5 Length: 2.0 cm. Diameter: 0.5 cm. Apex: Narrowly acute. Base: Fused. Texture (both surfaces): Smooth to glandular (see below). Pubescence: Present (glandular trichomes). Sepal color: Upper surface: RHS 143B (green). Lower surface: RHS 143B (green).
- *Pedicels*.—Angle: 15-25°. Length: 1.0 cm. Diameter: 0.3 cm. Texture: Smooth to glandular (glandular trichomes). Color: Distal portion is RHS 187A (grey-purple) and the bottom portion is RHS 143A (green).

*Reproductive organs*.—Stamens: Present. Number: 4 anthers with stamens fused at base to corolla. Filament: 4 (fused). Color: RHS 155D (white). Length: Two at 2.0 cm and two at 2.5 cm (measured from base of corolla). Diameter: 0.2 cm. Anther color: RHS 155D (white). Pollen amount: Sparse, with 3% pollen stainability. Pollen color: RHS 155D (white). Pistils: Number/flower: 1. Pistil length: 2.5 cm. Stigma: Color: RHS 155D (white). Shape: Bilabial and slightly recurved. Length: 0.2 cm. Diameter: 0.2 cm. Style: Color: RHS 155D (white). Length: 2.3 cm. Diameter: 0.1 cm. Ovary: Shape: Hypogenous, elliptic. Color: RHS 143A (green).

Fruit/seed set: None observed.

Disease and insect resistance: Disease and insect resistance is typical of the species.

COMPARISON WITH KNOWN CULTIVARS

When 'R12-2-1' is compared to the female parent 'RU64' (not patented), 'R12-2-1' has medium plant height and violet flowers, while 'RU64' has tall plant height and white flowers. When 'R12-2-1' is compared to the male parent '37-3-6-1' (not patented), 'R12-2-1' has medium plant height and violet flowers, while '37-3-6-1' has tall plant height and white flowers with violet corolla tube.

When 'R12-2-1' is compared to 'Purple Showers' (not patented), average plant height is 81 cm, significantly different to that of 'Purple Showers' with 107 cm. Average plant width of 'R12-2-1' is 73 cm, significantly different to that of 'Purple Showers' with 88 cm. Average number of stems of 'R12-2-1' is 62 cm, significantly different to 'Purple Showers' with 40. The length of the longest stem on 'R12-2-1' is 88 cm, significantly different to 'Purple Showers' with 121 cm. The average number of nodes on the longest stem of 'R12-2-1' is 18 cm, significantly different to 'Purple Showers' with 16. The average length of mature leaves of 'R12-2-1' is 8.5 cm, significantly different to 'Purple Showers' with 9.8 cm. The average width of mature leaves of 'R12-2-1' is 1.7 cm, significantly different to 'Purple Showers' with 1.1 cm. The average landscape performance of 'R12-2-1' (on a scale from 1 to 5) is 4.1, significantly different to 'Purple Showers' with 3.5.

When 'R12-2-1' is compared to 'R10-102' (U.S. Plant Pat. No. 24,422), average plant height is 81 cm, significantly different to that of 'R10-102' with 95 cm. Average plant width of 'R12-2-1' is 73 cm, significantly different to that of 'R10-102' with 84 cm. The length of the longest stem on 'R12-2-1' is 88 cm, significantly different to 'R10-102' with 109 cm. The average number of nodes on the longest stem of 'R12-2-1' is 18 cm, significantly different to 'R10-102' with 16. The average width of mature leaves of 'R12-2-1' is 1.7 cm, significantly different to 'R10-102' with 1.2 cm. The leaves on 'R12-2-1' with color RHS 147A and RHS 137B (on the adaxial and abaxial side of the lamina, respectively) are darker green than leaves on 'R10-102' with leaf color RHS 139A and RHS 137C (on the adaxial and abaxial side of the lamina, respectively). The average landscape performance of 'R12-2-1' (on a scale from 1 to 5) is 4.1, significantly different to 'R10-102' with 3.5.

I claim:

1. A new and distinct variety of *Ruellia* plant named 'R12-2-1' as illustrated and described herein.

* * * * *